(12) United States Patent
Igarashi

(10) Patent No.: US 10,307,044 B2
(45) Date of Patent: Jun. 4, 2019

(54) ENDOSCOPE ILLUMINATING OPTICAL SYSTEM

(71) Applicant: OLYMPUS CORPORATION, Hachioji-shi, Tokyo (JP)

(72) Inventor: Tsutomu Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/822,659

(22) Filed: Nov. 27, 2017

(65) Prior Publication Data

US 2018/0078127 A1 Mar. 22, 2018

Related U.S. Application Data

(63) Continuation of application No. PCT/JP2016/069911, filed on Jul. 5, 2016.

(30) Foreign Application Priority Data

Sep. 9, 2015 (JP) .................................. 2015-177420

(51) Int. Cl.
*A61B 1/00* (2006.01)
*A61B 1/05* (2006.01)
(Continued)

(52) U.S. Cl.
CPC ............. *A61B 1/06* (2013.01); *A61B 1/00096* (2013.01); *A61B 1/05* (2013.01); *A61B 1/0661* (2013.01);
(Continued)

(58) Field of Classification Search
CPC .............. A61B 1/00096; A61B 1/0016; A61B 1/00163; A61B 1/00167; A61B 1/0017;
(Continued)

(56) References Cited

U.S. PATENT DOCUMENTS 4,266,534 A * 5/1981 Ogawa ............... A61B 1/00096
359/721
4,584,988 A * 4/1986 Nishioka ............ A61B 1/00096
600/177
(Continued)

FOREIGN PATENT DOCUMENTS

JP 62143918 U 9/1987
JP 62287215 A 12/1987
(Continued)

OTHER PUBLICATIONS

Chinese Office Action (and English language translation thereof) dated Sep. 27, 2018 issued in counterpart Chinese Application No. 201680023858.7.
(Continued)

*Primary Examiner* — Ryan N Henderson
(74) *Attorney, Agent, or Firm* — Holtz, Holtz & Volek PC

(57) ABSTRACT

An endoscope illuminating optical system to be disposed at a front end of an insertion portion of an endoscope includes a lens formed by a transparent-resin molding having a function of a front-end frame, which is configured to be disposed at a front-end side of the insertion portion, and a light guide which is disposed adjacent to the lens. A surface of the lens facing the light guide is a composite concave surface in which two axisymmetric concave surfaces are overlapped, and has a gourd-shaped effective cross-section. An effective range of a distal end surface of the light guide has a shape of an ellipsoid, or an oval, or a gourd, and has a long axis in a longitudinal direction of the gourd-shaped effective cross-section of the surface of the lens facing the light guide side, and a short axis in a direction perpendicular to the long axis. The cross-section of the composite concave surface includes an end surface of the light guide.

2 Claims, 20 Drawing Sheets

(51) Int. Cl.
  *A61B 1/06*  (2006.01)
  *A61B 1/07*  (2006.01)
  *G02B 23/24* (2006.01)
  *G02B 23/26* (2006.01)

(52) U.S. Cl.
  CPC .......... *A61B 1/0669* (2013.01); *A61B 1/0676* (2013.01); *A61B 1/07* (2013.01); *G02B 23/243* (2013.01); *G02B 23/2469* (2013.01); *G02B 23/26* (2013.01); *A61B 1/0607* (2013.01)

(58) Field of Classification Search
  CPC ............ A61B 1/00172; A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; A61B 1/04; A61B 1/041; A61B 1/042; A61B 1/043; A61B 1/045; A61B 1/05; A61B 1/051; A61B 1/053; A61B 1/055; A61B 1/06; A61B 1/0607; A61B 1/0615; A61B 1/062; A61B 1/063; A61B 1/0638; A61B 1/0646; A61B 1/0653; A61B 1/0661; A61B 1/0669; A61B 1/0676; A61B 1/0684; A61B 1/0692; A61B 1/07; G02B 23/24; G02B 23/2407; G02B 23/2415; G02B 23/2423; G02B 23/243; G02B 23/2438; G02B 23/2446; G02B 23/2453; G02B 23/2461; G02B 23/2469; G02B 23/26
  See application file for complete search history.

(56) References Cited

U.S. PATENT DOCUMENTS

| | | | |
|---|---|---|---|
| 4,778,247 A * | 10/1988 | Carpenter | A61B 1/00096 362/574 |
| 4,802,460 A | 2/1989 | Ohkuwa et al. | |
| 4,824,225 A * | 4/1989 | Nishioka | G02B 3/04 359/718 |
| 4,952,040 A * | 8/1990 | Igarashi | G02B 3/04 359/708 |
| 2002/0161284 A1* | 10/2002 | Tanaka | A61B 1/00096 600/176 |
| 2008/0242935 A1 | 10/2008 | Inoue | |
| 2009/0306477 A1* | 12/2009 | Togino | A61B 1/00096 600/176 |
| 2010/0312057 A1 | 12/2010 | Konno | |
| 2011/0157574 A1 | 6/2011 | Kato et al. | |

FOREIGN PATENT DOCUMENTS

| | | |
|---|---|---|
| JP | 63239415 A | 10/1988 |
| JP | 05053063 A | 3/1993 |
| JP | 2003167203 A | 6/2003 |
| JP | 2008237790 A | 10/2008 |
| JP | 4741032 B2 | 8/2011 |
| WO | 2010113550 A1 | 10/2010 |
| WO | 2015015996 A1 | 2/2015 |

OTHER PUBLICATIONS

International Preliminary Report on Patentability (IPRP) dated Mar. 22, 2018 issued in counterpart International Application No. PCT/JP2016/069911.

International Search Report (ISR) and Written Opinion dated Sep. 20, 2016 issued in International Application No. PCT/JP2016/069911.

* cited by examiner

ENDOSCOPE ILLUMINATING OPTICAL SYSTEM

CROSS-REFERENCE TO RELATED APPLICATION

The present application is a continuation application of PCT/JP2016/069911 filed on Jul. 5, 2016 which is based upon and claims the benefit of priority from Japanese Patent Application No. 2015-177420 filed on Sep. 9, 2015; the entire contents of which are incorporated herein by reference.

BACKGROUND OF THE INVENTION

Field of the Invention

The present invention relates to an endoscope illuminating optical system.

Description of the Related Art

It is preferable that an endoscope intended for urinary organs, which is to be inserted transurethrally, is insertable into a urethra, and has an outer diameter not larger than 7 mm. In such manner, the endoscope for urinary organs has a diameter thinner than a diameter of an endoscope for alimentary track which is widely known for a medical examination of stomach or large intestine. Moreover, since the urinary organs are generally filled with urine, an optical design envisaged for in-water observation is necessary.

As a technology for in-water wide angle observation with an endoscope, an arrangement proposed in International Unexamined Patent Application Publication No. 2015/015996 for example, is available. In International Unexamined Patent Application Publication No. 2015/015996, it is signified that the medium of observation space in a case of observing the urinary organs with endoscope is a perfusion solution or urine of which water is the main constituent, and that it is reasonable to deem a refractive index of these media to be equivalent to the refractive index of water.

Furthermore, in International Unexamined Patent Application Publication No. 2015/015996, narrowing of an in-water angle of view with respect to an angle of view at the time of in-air observation has been cited. It has been signified that when the refractive index of water for a d-line is let to be 1.333, and an outer surface side of an endoscope objective optical system is let to be a flat surface, a relationship of the in-air angle of view and the in-water angle of view is shown as follows.

| In-air angle of view | 180° | 160° | 140° | 120° |
|---|---|---|---|---|
| In-water angle of view | 97.2° | 95.3° | 89.7° | 81.0° |

At the time of practical use of an endoscope for urinary bladder with the in-air angle of view of 120°, the in-water angle of view is narrowed to 81°. When an example of the endoscope for urinary bladder is cited, for exploring a pathological lesion inside the entire urinary bladder, an operator carries out a combined operation of bending a front end of the endoscope, inserting and removing an insertion portion, and twisting the insertion portion. When the in-water angle of view is narrow, a frequency of these operations is to be increased, and it becomes difficult to explore the pathological lesion inside the entire urinary bladder efficiently.

In such manner, in the endoscope that carries out the in-water observation, widening of the in-water angle of view has been desired. Securing a light-distribution of an illuminating optical system corresponding to the widened in-water angle of view becomes a challenging task when the in-water angle of view is to be widened. Moreover, in the endoscope for urinary bladder, a thin outer diameter, that can be inserted via the urethra, and mounting of a channel for treatment become indispensable. Consequently, an ability to mount in a narrow front-end space of endoscope is indispensable. Conventional endoscope illuminating optical systems, as an arrangement from a shape point of view, for securing the light-distribution, and mounting in particular, patent literatures from International Unexamined Patent Application Publication No. 2015/015996, International Unexamined Patent Application Publication No. 2010/113550, Japanese Patent Application Laid-open Publication No. 2008-237790, Japanese Utility Model Application Publication No. Sho 62-143918, Japanese Patent No. 4741032 Publication, Japanese Patent Application Laid-open Publication No. Sho 63-239415 have been known.

SUMMARY OF THE INVENTION

An endoscope illumination optical system to be disposed at a front end of an insertion portion of endoscope includes a lens formed by a transparent-resin molding having a function of a front-end frame, which is disposed at a front-end side of the insertion portion, and a light guide which is disposed adjacent to the lens, wherein a surface of the lens facing the light guide side is a composite concave surface in which two axisymmetric concave surfaces are overlapped, and has a gourd-shaped (similar to shape of numerical character '8') effective cross-section, and an effective range of the light guide has a shape of an ellipsoid, or an oval-shape or a gourd-shape end surface having a long axis in a longitudinal direction of the gourd-shaped effective cross-section on a side of the surface of the lens facing the light guide side, and a short axis in a direction perpendicular to the long axis, the cross-section of the composite concave surface includes an end surface of the light guide, the endoscope illuminating optical system satisfies the following conditional expressions (1), (2), and (3)

$$1.2 < Llgl/Llgs < 4 \quad (1)$$

$$0.25 < R'/\sqrt{(Llgl \times Llgs)} < 0.6 \quad (2)$$

$$0.4 < Lofs/(Llgl - Llgs) < 1.3 \quad (3)$$

where,

Llgl denotes the maximum length in a long-axis direction of the end surface of the light guide, Llgs denotes the maximum length in a short-axis direction of the end surface of the light guide, R' denotes a radius of curvature at a practical center of the axisymmetric concave surface, and Lofs denotes a distance between axes of the two axisymmetric concave surfaces.

BRIEF DESCRIPTION OF THE DRAWINGS

FIG. 1A is a cross-section in a short-axis direction, and FIG. 2B is a cross-section in a long-axis direction;

FIG. 5A shows an elliptical shape, FIG. 5B shows an oval shape, and FIG. 5C shows a gourd shape;

FIG. 6A shows an in-water observation state and FIG. 6B shows an in-air observation state;

FIG. 7A shows an in-water observation state and FIG. 7B shows an in-air observation state;

FIG. 9A is a cross-section in a short-axis direction and FIG. 9B is a cross-section in a long-axis direction;

FIG. 11A is a cross-section in a short-axis direction and FIG. 11B is a cross-section in a long-axis direction;

FIG. 13A is a cross-section in a short-axis direction and FIG. 13B is a cross-section in a long-axis direction;

FIG. 15A is a cross-section in a short-axis direction and FIG. 15B is a cross-section in a long-axis direction;

FIG. 17A is a cross-section in a short-axis direction and FIG. 17B is a cross-section in a long-axis direction;

FIG. 19A is a cross-section in a short-axis direction and FIG. 19B is a cross-section in a long axis direction.

DETAILED DESCRIPTION OF THE INVENTION

An endoscope illuminating optical system according to an embodiment will be described below in detail by referring to the accompanying diagrams. However, the present invention is not restricted to the embodiment described below.

Figure 1A:
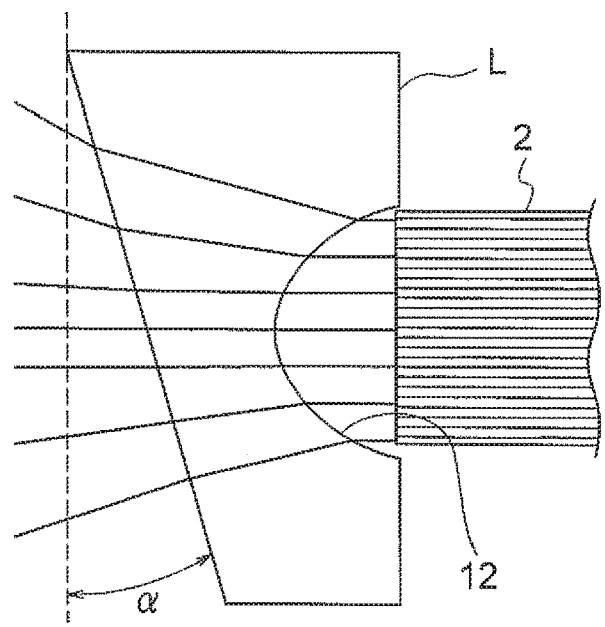
FIG. 1A and FIG. 1B are diagrams showing a cross-sectional shape of an endoscope illuminating optical system according to an embodiment of the present invention, where.
Figure 1B:
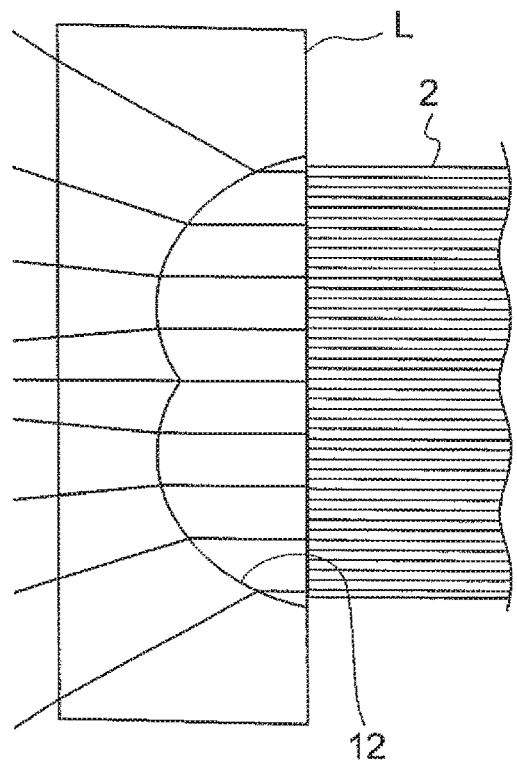

FIG. 1A and FIG. 1B show a cross-sectional arrangement in a short-axis direction and a cross-sectional arrangement in a long-axis direction respectively of the endoscope illuminating optical system of the present embodiment.

The endoscope illuminating optical system according to the embodiment includes a lens L which is disposed at a front-end side of an insertion portion, and a light guide 2 which is disposed adjacent to the lens L. A surface of the lens L facing toward the light guide 2 is a composite concave surface 12 in which two axisymmetric concave surfaces are overlapped, and has a gourd-shaped effective cross-section. An effective range of the light guide 2 has a shape of a non-circular end surface having a long axis in a longitudinal direction of the gourd-shaped effective cross-section on a side of the surface of the lens facing toward the light guide, and a short axis in a direction perpendicular to the long axis.

In contrast with non-axisymmetric concave surfaces (toric surfaces, anamorphic surfaces, and elliptical surfaces) known heretofore, the composite concave surface 12 of the present embodiment, in which two axisymmetric concave surfaces are overlapped, has an arrangement advantageous for widening the distribution of light.

In the conventional non-axisymmetric concave surfaces, the distribution of light in a long-axis direction, for which a divergence force in the long-axis direction is not enhanced, is degraded substantially as compared to the distribution of light in the short-axis direction. The reason being that, for letting the non-axisymmetric concave surfaces to cover an effective diameter of a light guide, it is necessary to weaken a curvature than that in the short-axis direction for which the effective diameter is small. As a result, the divergence force of the non-axisymmetric concave surfaces in the long-axis direction is weaker than the divergence force of the non-axisymmetric concave surfaces in the short-axis direction, and the distribution of light in the long-axis direction is degraded substantially as compared to the distribution of light in the short-axis direction.

Whereas, for the composite concave surface 12 formed by the axisymmetric concave surfaces, of the present invention, the divergence force in the short-axis direction and the divergence force in the long-axis direction are equal, and for securing the effective diameter in the long-axis direction, an amount of shifting of an axis of the composite concave surface 12 can be designed optimally as a parameter. Therefore, the composite concave surface 12 of the present embodiment is capable of improving the degradation of the distribution of light in the long-axis direction which has been a problem in the conventional arrangement.

The present embodiment will be described below in further details. To start with, a positional relationship of components of an illuminating optical system at the front end of the insertion portion, and other components mounted will be described below.

Figure 2:
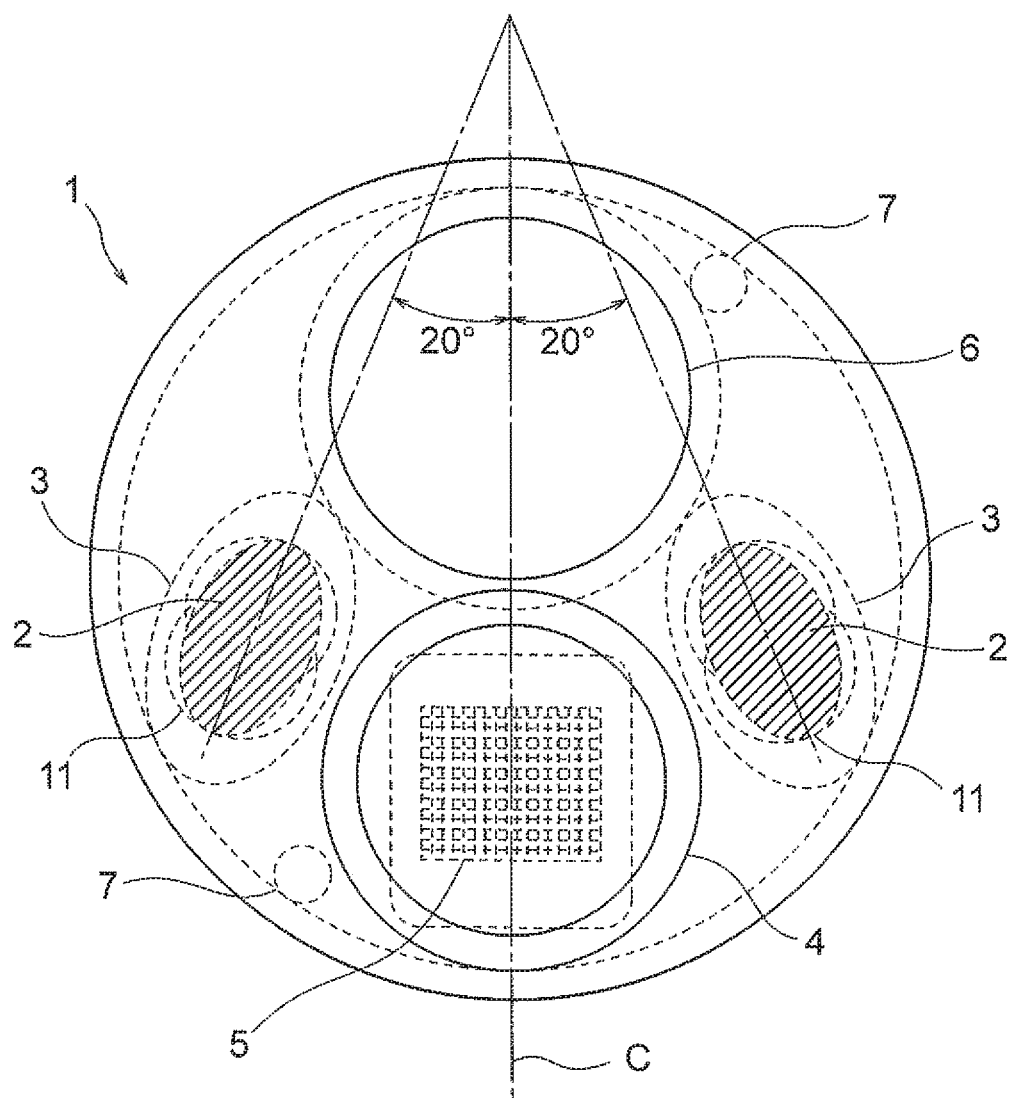
FIG. 2 is a diagram of a front-end portion of an endoscope having the endoscope illuminating optical system according to the embodiment, viewed from an object side.

FIG. 2 is a diagram of a front-end portion of an endoscope having the endoscope illuminating optical system of the embodiment. The light guide 2, an objective-lens frame 4 and a solid image pickup element 5, and a channel 6 are disposed inside a front-end portion 1 having a substantially circular cross-section.

Here, a signal cable, which is not shown in the diagram, of the solid image pickup element 5 and the light guide 2, and the channel 6 have an effect on a layout throughout the entire length of the insertion portion. Moreover, an angle wire 7 for a front-end bending mechanism is disposed at a position slightly away from the front-end portion 1.

A vertical direction of FIG. 2 corresponds to a vertical direction of an image. The solid image pickup element 5 outputs an image of a landscape-oriented aspect ratio in a leftward-rightward direction on a paper surface. When the channel 6 and the solid image pickup element 5 which are structural objects having a large cross-sectional area are disposed in a vertical direction (vertical direction on the paper surface) in a diameter of the front-end portion 1, a position at which the light guide 2 can be disposed is restricted to a space at left and right. Therefore, the light guide 2 which is divided into two at a front-end side is to be disposed.

At the front-end portion 1, a front-end frame 8 (FIG. 3) which holds various structural objects is formed by a transparent-resin molding which also serves a function of an illumination lens. A portion of the front-end frame 8, facing the light guide 2 is an illumination lens, and has a composite concave surface gourd-shaped cross-section 11 at an inner-surface side.

For letting light emerged from the light guide 2 to be incident assuredly on the composite concave surface gourd-shaped cross-section 11, it is preferable to make an arrangement such that the composite concave surface gourd-shaped cross-section 11 includes a cross-section of the light guide 2. Furthermore, light transmitted through the composite concave surface gourd-shaped cross-section 11 is emerged to an object space from an illumination-lens front-end surface effective range 3 determined in an optical design on an outer-surface side of the front-end frame 8.

Figure 3:
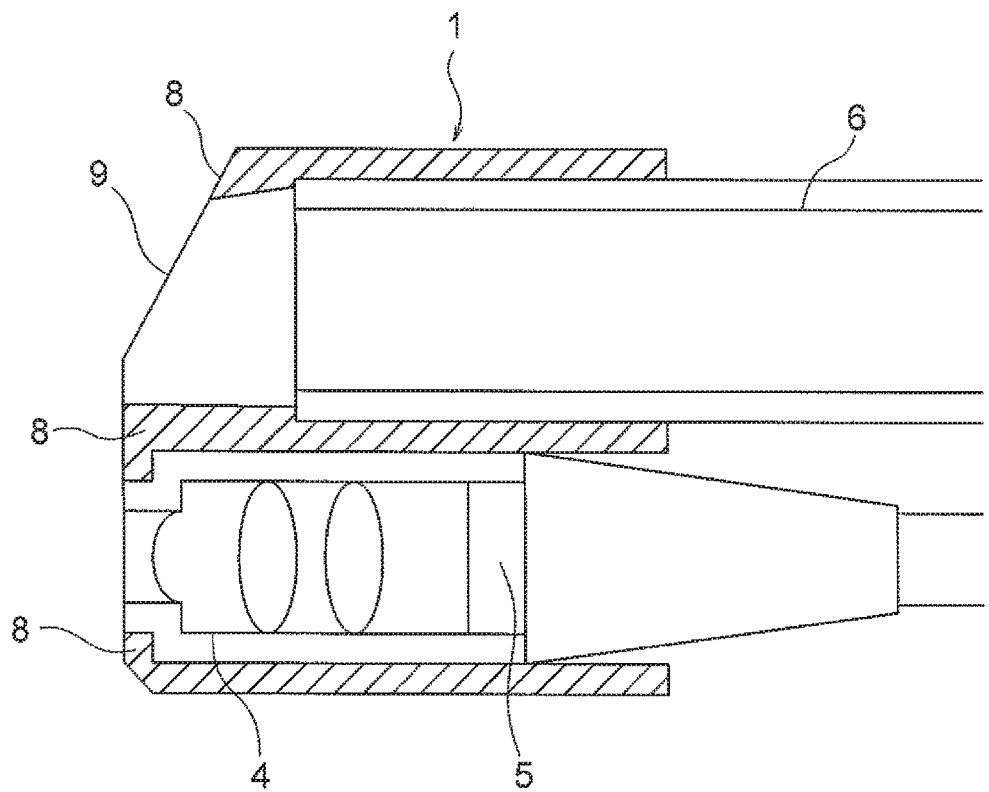
FIG. 3 is a cross-sectional view along an optical axial direction of the front end portion of the endoscope having the endoscope illuminating optical system according to the embodiment.

FIG. 3 is a horizontal cross-sectional view of a front-end portion of the endoscope having the endoscope illuminating optical system of the present embodiment, cut along a line (C-axis) connecting a center of the channel 6 and a center of the objective-lens frame 4. This is an arrangement in which the channel 6 and the objective-lens frame 4 are fixed to the front-end frame 8 made of the transparent-resin molding.

In view of the improvement in insertion into the urethra, a channel opening portion 9 is ramped such that the front-end frame 8 is tapered off. For letting it to be a smooth tapered shape by taking an angle of ramping as large as possible, it is necessary to separate apart the light guide 2 and the illumination-lens front-end surface effective range 3 from the channel opening portion 9. For this, the light guide 2 and the illumination-lens front-end surface effective range 3 are disposed at a relatively lower side in the cross-section in FIG. 2.

Figure 4:
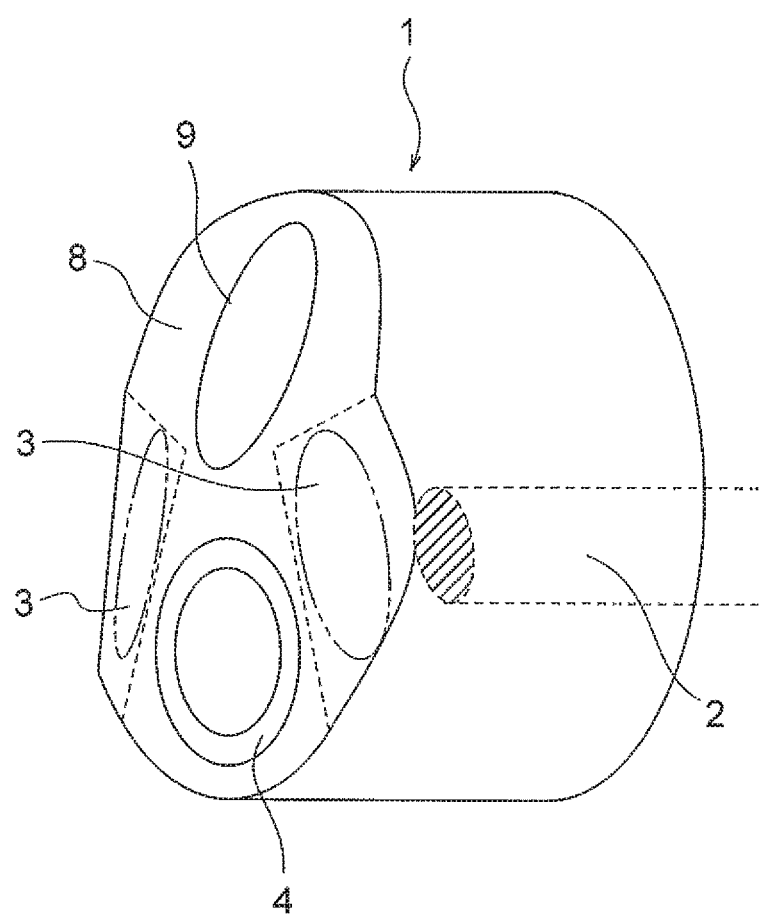
FIG. 4 is a perspective configuration view of the front-end portion of the endoscope having the endoscope illuminating optical system according to the embodiment, viewed from the object side.

FIG. 4 is a diagram showing a configuration of the front-end portion of the endoscope having the endoscope illuminating optical system of the embodiment, viewed obliquely from an object side. The front-end frame 8 has the ramp of the channel opening portion 9. Furthermore, for tapering the front-end portion 1 of the endoscope with an object of improving the insertion, the illumination-lens front-end surface effective range 3 is let to be inclined only by angle α (FIG. 1A).

In such manner, it is preferable to take into consideration a shape of a front-end surface of the front-end frame 8 at the time of disposing the components from a point of view of improvement in the insertion. In the arrangement shown in FIG. 2, the arrangement of the illumination-lens front-end surface effective range 3 and the light guide 2, including the shape of an inclined surface that includes the illumination-lens front-end surface effective range 3, is optimized.

In FIG. 2, the light guide 2 is an ellipsoid having a long axis thereof inclined by 20° with respect to the axis (C-axis) passing through the center of the channel 6 and the center of the objective-lens frame 4. The illumination-lens front-end surface effective range 3 is also an ellipsoid having an orientation same as that of the light guide 2.

For the illumination-lens front-end surface effective range 3, it is preferable to secure an effective area adequate for realizing a wide-angle light distribution while avoiding interference of the illumination-lens front-end surface effective range 3 with the channel opening portion 9 and the objective-lens frame 4 in the front-end portion 1. An area of the illumination-lens front-end effective range 3 is inadequate in a normal effective range of a circular shape.

Therefore, it is necessary to make the non-axisymmetric shape in portrait orientation as shown in FIG. 2 and FIG. 4. Moreover, the angle of inclination a of the illumination-lens front-end surface effective range 3 in the present embodiment is 15° in a short-axis direction of the light guide. By combination of the angle of inclination a and inclination of 20° with respect to the C-axis, it is possible to achieve an arrangement of the tapering toward the channel, thereby contributing to the improvement in the insertion as well.

Next, a cross-sectional shape of the light guide will be described below in detail. In the present embodiment, and end surface of the light guide 2 toward the front end of the insertion portion is let to be a non-circular shape having a long-axis direction and a short-axis direction. Accordingly, it is possible to improve a degree of freedom of arranging components at the front end of the insertion portion, and to make it easy to optimize a mounting efficiency.

Figure 5A:
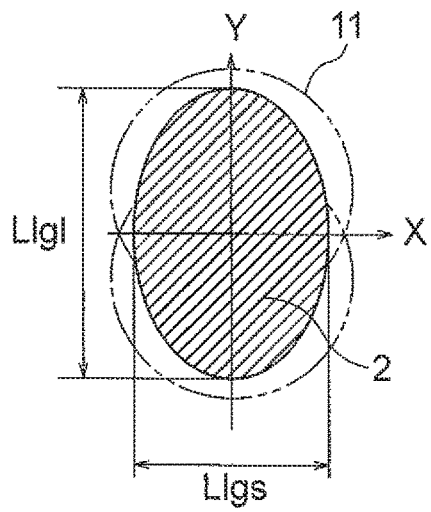
FIG. 5A, FIG. 5B, and FIG. 5C are diagrams showing a shape of an end surface of a light guide of the endoscope illuminating optical system according to the present embodiment, where.
Figure 5B:
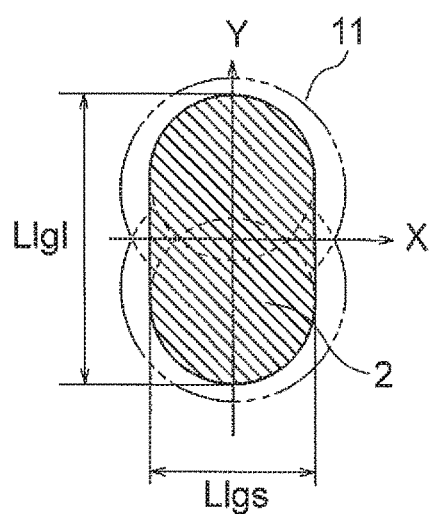
Figure 5C:
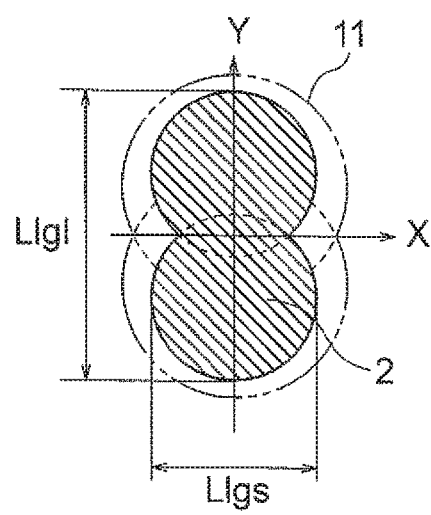

Here, an arrangement of various polygonal shapes and curved surfaces may be adopted as the non-circular shape having a difference in a length in a long-axis direction and a length in a short-axis direction. In the present embodiment, as shapes which have a comparatively easier geometrical definition, and which enable easy molding of the light guide 2, three types of shapes shown in FIG. 5A, FIG. 5B, and FIG. 5C are to be used. In FIG. 5A, FIG. 5B, and FIG. 5C, to indicate that an effective range of a composite concave surface includes an end surface of the light guide 2, the composite concave surface gourd-shaped cross-section 11 is shown to be combined.

The first type of the cross-sectional shape of the light guide is an ellipsoid as shown in FIG. 5A. Orthogonal axes X and Y in each of FIG. 5A, FIG. 5B, and FIG. 5C are local coordinates in the cross section of the light guide.

Generally, an ellipsoid is defined by two parameters which are a long radius and a short radius. In the present embodiment, to make consistent with the other two types of geometrical definitions, the ellipsoid in FIG. 1 will be defined by the maximum length in long-axis direction Llgl which is twice the long radius, and the maximum length in short-axis direction Llgs which is twice the short radius.

The second type of the cross-sectional shape of the light guide is an oval shape as shown in FIG. 5B. The oval shape in the present embodiment is a shape in which two circles having the same diameter are slid in a state of the circles overlapping partly, and circumferential portions of the two circles are joined by straight lines. Since the maximum length in short-axis direction Llgs is equal to the diameter of the circle, and the maximum length in long-axis direction Llgl is length obtained by adding a distance between the centers of the circles to the diameter, the shape is to be defined by using the maximum length in short-axis direction Llgs and the maximum length in long-axis direction Llgl.

The third type of the cross-sectional shape of the light guide is a gourd shape as shown in FIG. 5C. The gourd shape in the present embodiment is a shape in which two circles having the same diameter are slid and combined in a state of the circles overlapping partly. Similarly as for the oval shape, the shape is to be defined by using the maximum length in short-axis direction Llgs and the maximum length in long-axis direction Llgl.

With the three types of cross-sectional shapes of the light guide described above, it is possible to use effectively the effective range of the composite concave surface gourd-shaped cross-section 11, and can be used preferably in combination with the composite concave surface 12. In the present embodiment, the cross-sectional shape of the light guide is to be defined by the maximum length in short-axis direction Llgs and the maximum length in long-axis direction Llgl for each type of the shape, and is to be disposed in an absolute coordinate system of the insertion-portion space upon imparting arbitrary rotation thereto.

Next, details of the composite concave shape will be described below. For an endoscope having the endoscope illuminating optical system of the present embodiment, an in-air angle of view is more than 180° and the in-water angle of view is not less than 100°. Therefore, the light-distribution requirements are exacting as compared to a general endoscope for which the in-air angle of view is less than 170°. The surface of the lens L toward the light guide 2 is let to be a concave surface for evading various problems that arise due to a convex type, while diffusing light emerged from the light guide for securing a wide-angle light distribution.

With the convex type, problems such as a thermal safety of a living organism, thermal unfolding of resin at the time of mounting the transparent resin, and occurrence of unevenness due to projection of a light-guide fiber, accompanied by an effect of focusing and imaging, arise. Therefore, the arrangement of the present embodiment has a concave shape which suppresses an occurrence of such problems. Furthermore, by combining two axisymmetric concave surfaces by overlapping, and forming a gourd-shaped cross-section toward the light guide 2, the most appropriate design by combining with the light guide of a non-axisymmetric cross-sectional shape is made possible.

The axisymmetric concave surface may be any of a spherical surface and an aspheric surface. A definitional expression in the present embodiment which is applicable to both the spherical axisymmetric concave surface and the aspheric axisymmetric concave surface is shown below. As local coordinates of a plane, when an optical axial direction is let to be a Z-axis, and an axis perpendicular to the Z-axis is let to be a Y-axis, the definitional expression for the axisymmetric spherical surface in a Y-Z cross-section is shown by numerical expression (5).

[Numerical expression 1]

$$Z(Y) = \frac{Y^2/R}{1+\sqrt{1-(1+K) \times Y^2/R^2}} + \sum_{n}\{A_{2n} \times Y^{2n}\} \quad (5)$$

Here,
Y denotes Y-coordinate,
Z(Y) denotes Z-coordinate obtained as a function of Y,
R denotes a radius of curvature of a center of a spherical surface term in the Y-Z cross-section,
K denotes a coefficient which determines quadratic surface characteristics in the Y-Z cross-section,
n denotes an integer not smaller than 1, and
$A_{2n}$ denotes a coefficient by order of aspheric polynomial terms in the Y-Z cross-section.

In numerical expression (5), by letting K=0, it becomes a spherical surface when the polynomial term is also 0. In such manner, numerical expression (5) can depict both of an aspheric surface and a spherical surface.

By combining by axially sliding the two concave surfaces defined by numerical expression (5), it is possible to form a composite concave surface having a gourd-shaped cross-section. The composite concave surface gourd-shaped cross-section 11 in FIG. 2 corresponds to the composite concave surface.

Since a direction of axially sliding the composite concave surface 12 coincides with a long-axis direction of the composite concave surface gourd-shaped cross-section 11, the direction of axially sliding the composite concave surface 12 and a long-axis direction of the light guide 2 are to be adjusted in the same direction. Furthermore, by designing parameters such that the composite concave surface gourd-shaped cross-section 11 includes the cross-section of the light guide 2, it is possible to diffuse light emerged from the light guide 2 at the composite concave surface 12, without the light being polarized. The combination of the composite concave surface 12 and the light guide 2 designed in such manner is disposed at both left side and right side of the C-axis passing through the channel 6 and the center of the objective-lens frame 4 in the absolute coordinate system of the insertion portion space.

Optimization of the light distribution is carried out by setting appropriate parameters in numerical expression (5) of the axisymmetric concave surface. In the composite concave surface 12, it is possible to apply a strong divergence force which is optimized with respect to the maximum length in short-axis direction of the light guide 2. In this case, in a single concave lens, an effective diameter with respect to the maximum length in long-axis direction Llgl of the light guide 2 becomes inadequate. For the composite concave surface 12, an optimum design in which the maximum length in long-axis direction Llgl is included, letting an amount of axial slide as a parameter, is possible.

Moreover, in the axisymmetric concave surface, there is no difference in the divergence force due to orientation, and the divergence force in the long-axis direction is equal to the divergence force in the short-axis direction. Furthermore, since an angle of refraction for the axisymmetric concave surface becomes larger at a peripheral portion than an angle of refraction at a central portion, by separating the axisymmetric surfaces at an appropriate axial distance, it is possible to improve a proportion of light refracted at a peripheral portion of the concave surface, and to improve divergence in the long-axis direction.

Accordingly, the composite concave surface of the present embodiment is capable of improving the degradation of the distribution of light in the long-axis direction. Although the effect can be achieved even with the axisymmetric concave surfaces which are spherical, letting the axisymmetric concave surfaces to be aspheric is preferable as the degree of freedom of controlling the light-distribution characteristics improves.

It is possible to mold the composite concave surface 12 by using a mold. It is possible to use a mold machining method also, for the axisymmetric concave surfaces by letting the mold for molding the composite concave surface to have two parts. Firstly, a convex surface which transfers the axisymmetric concave surfaces defined by numerical expression (5) to a base material in the form of a pin is prepared. Next, an outer circumferential portion of the base material in the form of a pin is cut in the form of a flat surface and is let to be a pin-shaped mold. Moreover, two pin-shaped molds are fabricated, and by overlapping the flat surface portion cut from the outer circumferential portion, a mold for transferring the composite concave surface having two convex surfaces is completed. Since axisymmetric rotary cutting is possible for convex surface machining on the base material in the form of a pin, it is possible to fabricate a mold with accuracy higher than that of a non-axisymmetric surface shape.

With the arrangement described above, in the present embodiment, it is possible to realize an illuminating optical system in which the mountability is secured while improving a light-distribution performance which has been a problem in the conventional technology.

Moreover, according to a preferable aspect of the present embodiment, in addition to the abovementioned arrangement, it is desirable to satisfy the following conditional expressions (1), (2), and (3) related to parameters of the light guide and the composite concave surface.

$$1.2 < Llgl/Llgs < 4 \quad (1)$$

$$0.25 < R'/(Llgl \times Llgs) < 0.6 \quad (2)$$

$$0.4 < Lofs/(Llgl - Llgs) < 1.3 \quad (3)$$

where,

Llgl denotes the maximum length in a long-axis direction of an end surface of the light guide, Llgs denotes the maximum length in a short-axis direction of the end surface of the light guide, R' denotes a radius of curvature at a practical center of the axisymmetric concave surfaces, and Lofs denotes a distance between axes of the two axisymmetric concave surfaces.

Conditional expression (1) is a condition for setting appropriately a ratio of the maximum length in the long-axis direction of the end surface of the light guide and the maximum length in the short-axis direction of the end surface of the light guide. As mentioned above, since the light guide is let to have a non-circular shape for improving the degree of freedom of component arrangement at the front end of the insertion portion, and optimizing the mounting efficiency, Llgl/Llgs takes a range significantly larger than 1.

When a value falls below a lower limit value of conditional expression (1), it is not desirable since the light distribution is inadequate by and large, as the end surface of the light guide is close to be circular-shaped. Although it is possible to optimize the divergence force of the axisymmetric concave surface with respect to the Llgs in the short-axis direction Llgs, the Llgs being relatively large, a light beam in the short-axis direction becomes thick by and large. Accordingly, light cannot be used effectively in the short-axis direction in which the effective range of the illumination-lens front-end surface effective range 3 is small, and since the light distribution in the short-axis direction cannot be improved, it is not desirable. Moreover, in a state in which the end surface of the light guide is close to be circular-shaped, since it is not possible to have a large distance between the axisymmetric surfaces, the diffusivity in the long-axis direction cannot be improved, and it is not desirable.

When an upper limit value of conditional expression (1) is exceeded, as an attempt is made to enhance adequately the divergence force of the axisymmetric concave surfaces by optimizing to Llgs, the effective diameter of the axisymmetric concave surface becomes small. Even when the distance between the axis Lofs of the axisymmetric concave surfaces is made large, it becomes difficult to cover Llgl, or even when Lofs has covered Llgl, Lofs cannot cover Llgs at a dented portion of the gourd-shaped cross-section. Accordingly, for making the gourd-shaped cross-section cover the end surface of the light guide assuredly, the effective diameter of the axisymmetric concave surface has to be secured by lowering the divergence force of the axisymmetric concave surface, as a result of which the light-distribution becomes inadequate, and therefore it is not desirable.

Conditional expression (2) is a condition for widening the light distribution by making the radius of curvature at a practical center of the axisymmetric concave surfaces adequately small with respect to an average diameter of the end surface of the light guide. Here, R' is the radius of curvature at a practical center of the axisymmetric concave surfaces by combination of secondary order components converted from coefficient $A_2$ which is a secondary component of a spherical surface term and a polynomial, and a definition thereof is indicated by numerical expression (6)

[Numerical expression 2]

$$R' = R/(1 + 2 \times A_2 \times R) \quad (6)$$

In the present embodiment, the divergence force of the axisymmetric concave surfaces has an effect on the light distribution in all orientations. The light-distribution requirements, compared to those in air, are even more exacting in water in which light is not diffused as in air. Therefore, it is significant to keep a diffusion force of the axisymmetric concave surfaces as high as possible. In a case in which the axisymmetric concave surfaces are spherical and the end portion of the light guide is circular, when R' is about half of the diameter of the light guide, the curvature becomes the maximum, and the end surface of the light guide cannot be covered by R' smaller than this. Therefore, in a case of a normal spherical and circular light guide, it is preferable to let R' to be about half of the diameter of the light guide.

The end surface of the light guide of the present embodiment being non-axisymmetric, $\sqrt{(Llgl \times Llgs)}$ is used as a parameter equivalent to an average diameter of the light guide as a denominator in conditional expression (2), and a proportion with the R' is regulated.

Even in the embodiment, in a case in which a value of conditional expression (2) is 0.5, R' is equivalent to half of the average diameter of the light guide, and signifies to have adequately high diffusivity. Furthermore, in a case in which the axisymmetric concave surface is an aspheric surface, it is possible to make R' even smaller, and to achieve a stronger diffusion force even under a restriction of covering the end surface of the light guide by smalling a center of curvature and weakening a peripheral curvature.

In a case in which a value falls below a lower limit value of conditional expression (2), where the axisymmetric concave surfaces inevitably become an aspheric surface, for covering Llgs, the curvature has to be weakened substantially in a peripheral portion of the concave surface, and light cannot be diffused adequately in a peripheral portion of an in-water wide-angle visual field, and it is not possible to realize wide-angle light distribution, and therefore it is not desirable.

In a case in which, an upper limit value of conditional expression (2) is exceeded, contrary to what was mentioned above, the divergence force at a central portion of the concave surface being weak, a luminance of light emerged in a direction of center of a visual field becomes high, and a peripheral portion becomes relatively darker with respect to the center of the visual field, and the wide-angle light distribution cannot be achieved, and therefore it is not desirable.

Conditional expression (3) is a condition for setting appropriately the distance between the axes of the axisymmetric concave surfaces in the composite concave surface. Since the distance between the axes Lofs of the axisymmetric concave surfaces has an effect on a flat property of the cross-section of the light guide, it is preferable to set Lofs with an appropriate proportion with respect to (Llgl–Llgs) which is a difference between lengths of the cross-section of the light guide in various directions.

When a value falls below a lower limit value of conditional expression (3), Lofs becomes excessively small relatively, with respect to the flat property of the cross-section of the light guide, and tends to be inadequate from a point of view of covering a side of the cross-section of the light guide in the long-axis direction. In this case, the design has to be such that the long-axis direction of the cross-section of the light guide is covered by widening the effective diameter by weakening the curvature of the axisymmetric concave surfaces.

When an upper limit value of conditional expression (3) is exceeded, Lofs becomes excessively large relatively, with respect to the flat property of the cross-section of the light guide, and is susceptible to be not capable of covering the end surface of the light guide at the dented portion of the gourd-shaped cross-section. In this case also, the design has to be such that the cross-section of the light guide is covered even in the dented portion of the gourd-shaped cross-section, by widening the effective diameter by weakening the curvature of the axisymmetric concave surfaces. Accordingly, in any of the cases of either the value falling below the lower limit value or exceeding the upper limit value, the divergence force of the axisymmetric concave surfaces is lowered, and it is not possible to realize the wide-angle light distribution, and therefore it is not desirable.

Moreover, according to a preferable aspect of the present embodiment, in addition to the abovementioned arrangement, it is desirable that the axisymmetric concave surfaces which form the composite concave surface include aspheric surfaces, and satisfy the following conditional expression (4).

$$(Z(H)-Zr'(H))/R'<-0.01 \quad (4)$$

where, it is a case in which $H=0.9 \times R'$,

H denotes a height from an optical axis at the axisymmetric concave surfaces,

Z(H) denotes an amount of displacement in an optical axial direction at the height H of the axisymmetric concave surfaces, and Zr'(H) denotes an amount of displacement in the optical axial direction at the height H on a spherical surface of the radius of curvature of the practical center R'.

In this case, H is a height of each axisymmetric concave surface which forms the composite concave surface, from an optical axis passing through the center of curvature, and is equivalent to Y in a definition of the axisymmetric aspheric surface of numerical expression (5). Moreover, Z(H) is equivalent to Z(Y) in numerical expression (5), and is to be computed by using numerical expression (5). Furthermore, Zr'(H) is the amount of displacement in the optical axial direction assuming a spherical surface of R' computed from numerical expression (4) with the radius of curvature at the practical center of the axisymmetric concave surfaces, and is to be computed by using numerical expression (7) obtained by eliminating the parameter related to the aspheric surface from numerical expression (5).

[Numerical expression 3]

$$Zr'(Y) = \frac{Y^2/R'}{1+\sqrt{1-Y^2/R'^2}} \quad (7)$$

According to the abovementioned definition, (Z(H)–Zr'(H)) is equivalent to a difference in an amount of displacement in Z-direction of the aspheric surface and an amount of displacement in Z-direction of the spherical surface. The axisymmetric concave surfaces of the present embodiment are defined as a positive value, and Z coordinate at a position away from the optical axis essentially has a positive amount of displacement.

Accordingly, it signifies that when (Z(H)–Zr'(H)) is positive, the displacement by the aspheric surface acts in a direction of deepening the concave surface, and when (Z(H)–Zr'(H)) is negative, the displacement by the aspheric surface acts in a direction of shallowing the concave surface. By standardizing (Z(H)–Zr'(H)) in conditional expression (4), conditional expression (4) is let to be a condition which indicates the degree of effect of the displacement of the spherical surface.

Since it is significant to achieve both the improvement in light distribution in the peripheral portion of the wide-angle visual field and securing the effective diameter that covers the end surface of the light guide, it is preferable to let to be an aspheric surface that weakens the curvature in the peripheral portion of the concave surface, by letting the value of conditional expression (4) to be negative.

When an upper limit value of conditional expression (4) is exceeded, an effective effect of letting it to be an aspheric surface cannot be achieved, and it is difficult to improve the light distribution upon covering the cross-section of the light guide, and therefore it is not desirable.

The arrangement of the endoscope illuminating optical system has been described above in detail. Here, a desirable arrangement of the front end of the insertion portion of the present embodiment including a layout of the front end of the insertion portion described above by using FIG. 1 to FIG. 4 is summed up below.

In the endoscope which has in the front end of the insertion portion thereof, the objective optical system, the channel 6, not less than two light guides 2, and the illuminating lens L which is disposed adjacent to the object side of the light guide 2, it is desirable that the surface of the illumination lens L facing the light guide is the composite concave surface 12 in which two axisymmetric concave surfaces are overlapped, and has a gourd-shaped effective cross-section 11, and the effective range of the light guide has a shape of the non-circular end surface having the long axis in the longitudinal direction of the gourd-shaped effective cross-section on the side of the surface of the illumination lens, and the short axis in a direction perpendicular to the long axis, and when the axis connecting the center of the objective-lens frame 4 (objective optical system) and the center of the channel 6 is let to the C-axis, the long axis of each light guide is inclined by not more than 30° with respect to the C-axis, and one or more than one illuminating system each, is disposed on each of the left and right side of the line of the C-axis, and satisfy conditional expressions (1) to (3). Furthermore, in a case of using the aspheric surface, it is desirable to have an arrangement that satisfies conditional expression (4).

(Description of Objective Optical System)

Prior to examples of the endoscope illuminating optical system, an arrangement of an objective optical system that is to be combined commonly in each example will be described below.

Figure 6A:
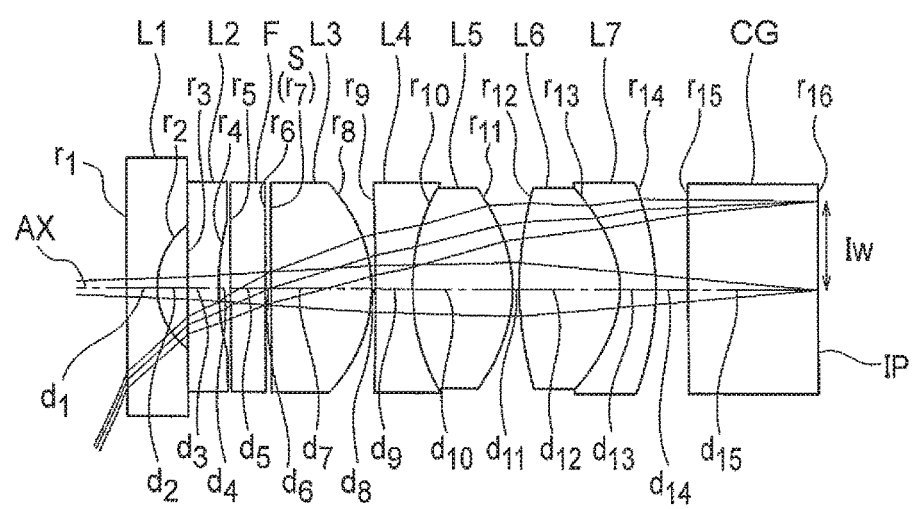
FIG. 6A and FIG. 6B are diagrams, each showing a lens arrangement of an objective optical system in an endoscope, where.
Figure 6B:
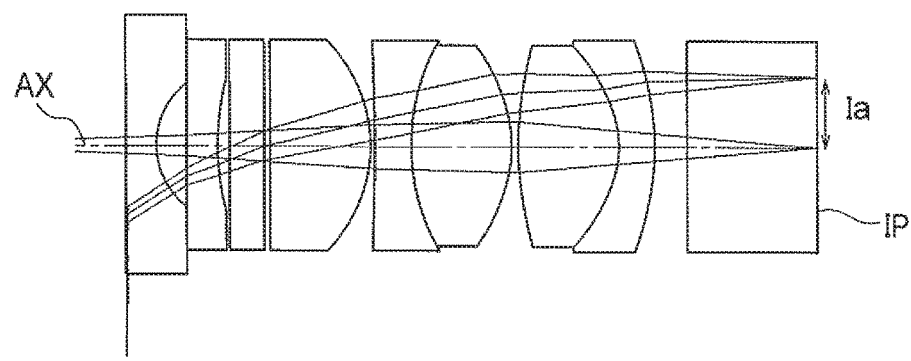

FIG. 6A shows an optical path and a lens cross-sectional view in water, of the objective optical system. FIG. 6B shows an optical path and a lens cross-sectional view in air of the objective optical system. The objective optical system includes in order from an object side, a planoconcave negative lens L1 of which an object side is a plane surface, a planoconcave negative lens L2 of which an object side is a plane surface, a plane parallel plate F1, a planoconvex positive lens L3 of which an object side is a plane surface, a biconcave negative lens L4, a biconvex positive lens L5, a biconvex positive lens L6, a C-axis negative meniscus lens L7, and a cover glass CG. Here, the biconcave negative lens L4 and the biconvex positive lens L5 are cemented. The biconvex positive lens L6 and the negative meniscus lens L7 are cemented.

An aperture stop S is disposed on an object-side surface of the planoconvex positive lens L3.

Numerical data for objective optical system is shown below. Regarding symbols, r denotes a radius of curvature of each lens surface, d denotes a distance between two lens surfaces, nd denotes a refractive index of each lens for a d-line, vd denotes Abbe's number for each lens, Fno denotes an F-number, and a focal length is a value for the d-line. Moreover, STO denotes an aperture stop, and IP denotes an image plane.

Example

| | | Unit mm | | |
|---|---|---|---|---|
| | | Surface data | | |
| Surface no. | r | d | nd | vd |
| 1 | ∞ | 0.25 | 1.76820 | 71.79 |
| 2 | 0.639 | 0.27 | | |
| 3 | ∞ | 0.25 | 2.00330 | 28.27 |
| 4 | 1.961 | 0.11 | | |
| 5 | ∞ | 0.30 | 1.52134 | 74.98 |
| 6 | ∞ | 0.03 | | |
| 7 | ∞(STO) | 0.87 | 2.00330 | 28.27 |
| 8 | −1.243 | 0.05 | | |
| 9 | −9.813 | 0.30 | 2.00330 | 28.27 |

-continued

| | | Unit mm | | |
|---|---|---|---|---|
| 10 | 1.717 | 0.86 | 1.72916 | 54.68 |
| 11 | −1.345 | 0.05 | | |
| 12 | 2.838 | 0.87 | 1.48749 | 70.23 |
| 13 | −1.108 | 0.30 | 1.92286 | 18.90 |
| 14 | −2.439 | 0.28 | | |
| 15 | ∞ | 1.10 | 1.51633 | 64.14 |
| 16 | ∞(IP) | | | | focal length: 0.56 mm
Fno.: 4.153
object distance in water: 9 mm
maximum outer diameter of lens: φ 2.2 mm

| image height and angle of view at the time of in-water observation: | | |
|---|---|---|
| | Image height (mm) | Angle of view (°) |
| Diagonal | 0.751 | 129.4 |
| Horizontal | 0.706 | 118.7 |
| Vertical | 0.482 | 76.3 |

Here, Iw in FIG. 6A is the image height in a diagonal direction in the in-water observation state, and is 0.751 mm. This image height is assumed to be matched with an effective image pickup area of the solid image pickup element, and the entire effective image pickup area of the solid image pickup element is to be used in the in-water observation state. The in-water angle of view at this time is 129.4° which is an extremely wide angle for the in-water observation, and it is possible to observe an object which is in water, by using the entire effective image pickup area of the solid image pickup element.

Whereas, by a surface nearest to object being a plane surface in the in-air observation state, only rays having the in-air angle of view of up to 180° can be incident on the lens. A principal light ray which is incident almost parallel to a plane surface nearest to object forms an image at a position lower than Iw on the image plane, and Ia which is equivalent to the maximum image height in air becomes 0.5995 mm. Accordingly, in the in-air observation state, an image achieved is an image in which the effective image pickup area of the solid image pickup element is used partially, and there is no problem with regard to the practical use in an endoscope intended for observation in air.

Figure 7A:
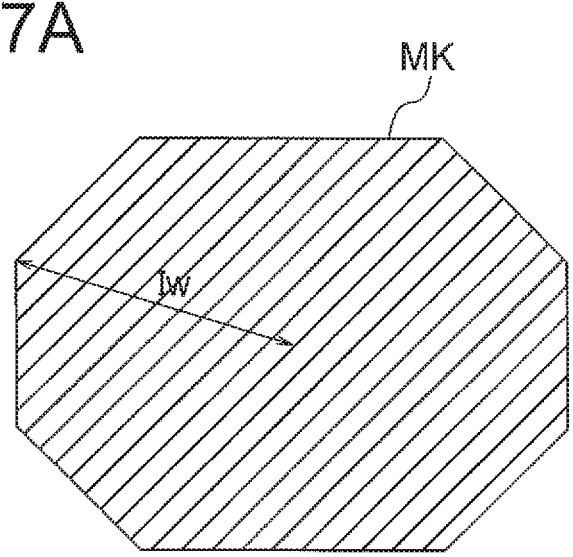
FIG. 7A and FIG. 7B are conceptual diagrams showing an imaging range of an in-water observation and an in-air observation, where.
Figure 7B:
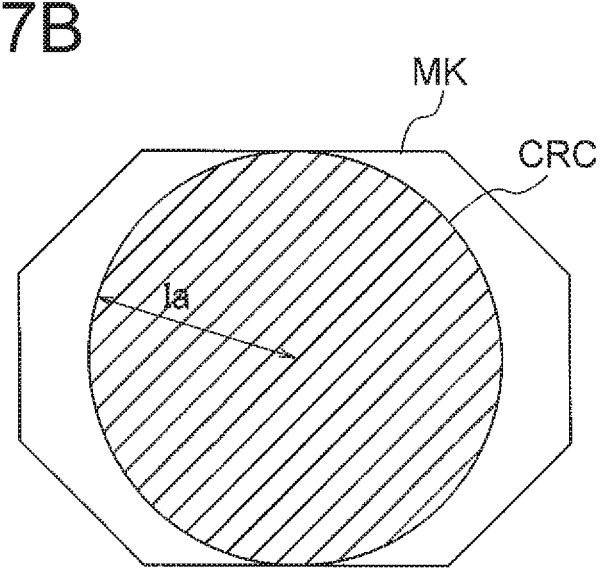

FIG. 7A and FIG. 7B are diagrams showing an imaging range of the in-water observation and in-air observation respectively. FIG. 7A and FIG. 7B are diagrams showing that the effective image pickup area in the in-air observation state becomes narrower than the effective image pickup area in the in-water observation state as described above.

FIG. 7A shows an image pickup area on the solid image pickup element in the in-water observation state. The diagram indicates that by using an octagonal electrical field mask, it is possible to use practically the entire effective image pickup area in an octagonal mask MK shown by hatched lines. The maximum image height in the octagonal mask MK is Iw.

FIG. 7B shows the image pickup area on the solid image pickup element in the in-air observation state. A circle CRC having a radius Ia shown by hatched lines becomes the image pickup area in the in-air observation state, and an area with no hatched lines between the octagonal mask MK and the circle CRC becomes an optically ineffective area in which no object image is formed.

According to such objective optical system, a wide-angle observation is possible even in the in-water state when the surface nearest to object is a plane surface. Furthermore, it is preferable that the object side is a plane surface, as no special arrangement is required in order to cope with a flare which is caused due to light from an illuminating optical system being incident directly, and there are no unnecessary restrictions on the arrangement of the illuminating optical system. A lens having the maximum lens outer diameter in the objective optical system is a lens at an object side end, and the maximum lens outer diameter is ϕ 2.2 mm. Even when combined with a channel and a bending mechanism having an inner diameter of ϕ 2.2 mm which is necessary as a cystoscope, it is possible to realize an endoscope with a front-end portion having an outer diameter less than ϕ 7 mm.

Next, various data of an illuminating optical system for endoscope according to each example is shown in table 1 and table 2 below.

All illumination lenses in the examples are formed of polysulfone (refractive index for d-line=1.635), and an outer-surface side shape thereof is a plane surface inclined by 15° in a long-axis direction of the light guide. Moreover, a central thickness of the illumination lens is 0.25 mm, and similarly as the light guide, the rotational orientation of the long axis with respect to the C-axis connecting the center of the objective-lens frame 4 (objective optical system) and the center of the channel 6 is 20°. Furthermore, an effective diameter of an outer-surface side in the long-axis direction is 2.2 mm, and an effective diameter of the outer-surface side in the short-axis direction is 1.6 mm.

Moreover, in an example for comparison, the combination is let to be a combination of a concave spherical surface lens and a circular light guide which can be mounted in the same space as of each example, and a central illuminance of an

TABLE 1

|  | | Light guide | | Type of axisymmetric concave surfaces | Concave surface | | | | |
|---|---|---|---|---|---|---|---|---|---|
|  | Cross sectional shape | Llgl [mm] | Llgs [mm] | | R [mm] | Aspheric surface coefficient * 0 when not mentioned | Depth [mm] | Lofs [mm] | R' [mm] |
| Example 1 | ellipsoid | 1.27 | 0.7 | aspheric surface | 0.465 | K = 0, A2 = 0.35, A4 = 2 | 0.4 | 0.45 | 0.351 |
| Example 2 | oval | 1.27 | 0.7 | aspheric surface | 0.465 | K = 0, A2 = 0.35, A4 = 2 | 0.4 | 0.45 | 0.351 |
| Example 3 | gourd shaped | 1.15 | 0.7 | aspheric surface | 0.465 | K = 0, A2 = 0.35, A4 = 2 | 0.4 | 0.45 | 0.351 |
| Example 4 | oval | 1.1 | 0.8 | aspheric surface | 0.45 | K = 0, A2 = 0.4 | 0.4 | 0.3 | 0.331 |
| Example 5 | oval | 1.45 | 0.6 | aspheric surface | 0.44 | K = 0, A2 = 0.4 | 0.44 | 0.6 | 0.325 |
| Example 6 | oval | 1.55 | 0.55 | aspheric surface | 0.46 | K = 0, A2 = 0.45 | 0.44 | 0.7 | 0.320 |
| Example for comparison | circular | (0.74) | (0.74) | spherical surface | 0.53 | — | 0.161 | — | 0.530 |

TABLE 2

|  | Horizontal direction 55° light distribution | Vertical direction 35° light distribution | Center illumination ratio | Exp 1 | Exp 2 | Exp 3 | Exp 4 |
|---|---|---|---|---|---|---|---|
| Example 1 | 17.2% | 54.5% | 100% (reference) | 1.814 | 0.372 | 0.789 | −0.056 |
| Example 2 | 17.9% | 57.9% | 103.5% | 1.814 | 0.372 | 0.789 | −0.056 |
| Example 3 | 17.3% | 52.8% | 98.3% | 1.643 | 0.391 | 1.000 | −0.056 |
| Example 4 | 15.4% | 50.8% | 103.4% | 1.375 | 0.353 | 1.000 | −0.117 |
| Example 5 | 17.4% | 76.1% | 93.6% | 2.417 | 0.349 | 0.706 | −0.116 |
| Example 6 | 15.2% | 87.1% | 91.6% | 2.818 | 0.352 | 0.700 | −0.122 |
| Example for comparison | 2.2% | 28.1% | 123.0% | 1.000 | 0.716 | — | 0 |

In the above Table, "Exp" denotes "Expression".

In table 1, a rotational orientation of the long axis of the light guide with respect to the C-axis connecting the center of the objective-lens frame 4 (objective optical system) and the center of the channel 6 of the two endoscope illuminating optical systems in each example is 20° as shown in FIG. 2. Coordinates of the center of the light guide with respect to the center of the objective optical system are (2.067, 0.752) and (−2.067, 0.752).

object surface is let to be of the same level as in each example having the lowest illuminance.

In other words, the light guide in the example for comparison is circular-shaped, and a diameter thereof is let to be 0.74 mm, and center coordinates (mm) with respect to a center of the objective optical system are let to be (2.067, 0.752) and (−2.067, 0.752). A material, an outer-side surface shape, a central thickness, and an effective diameter of an outer-surface side of an illumination lens in the example for comparison are similar to those in each example.

Figure 8:
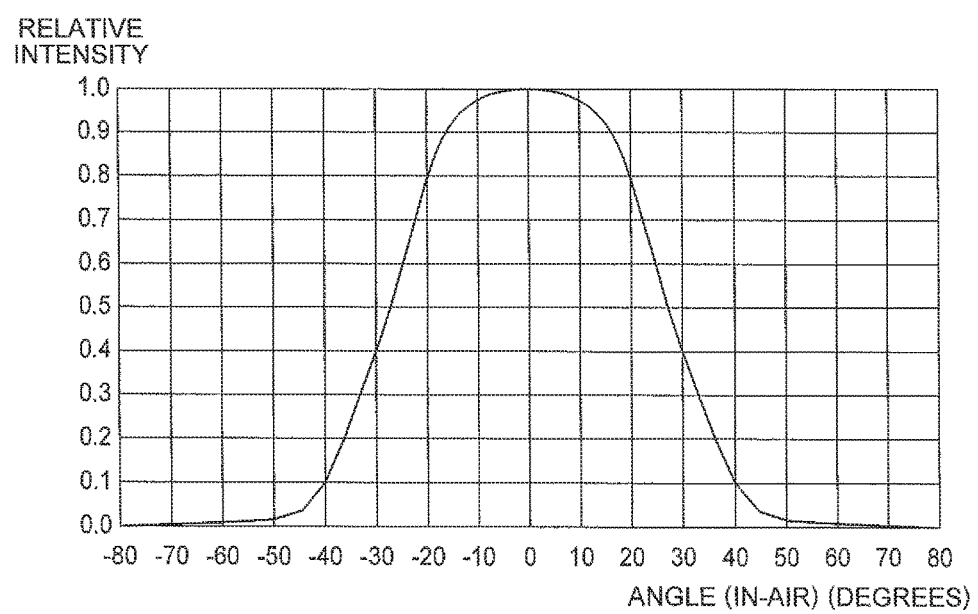
FIG. 8 is a graph showing a spherical light distribution of light emerged in air from a light guide in each example.
Figure 9A:
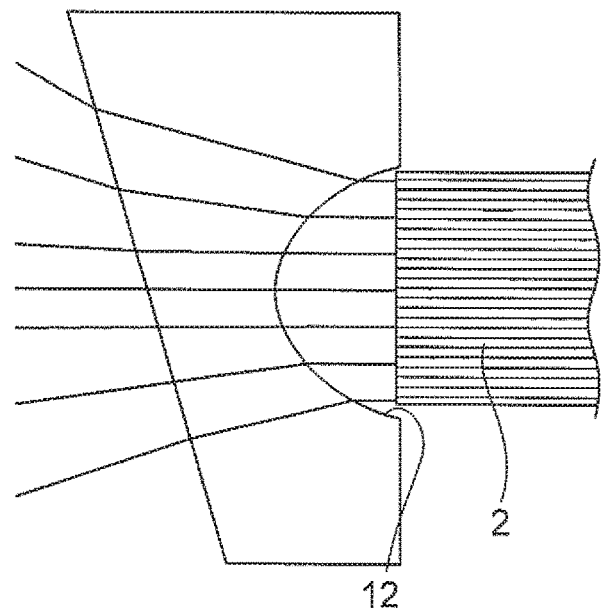
FIG. 9A and FIG. 9B are diagrams showing a cross-sectional shape of an endoscope illuminating optical system according to an example 1, where.
Figure 9B:
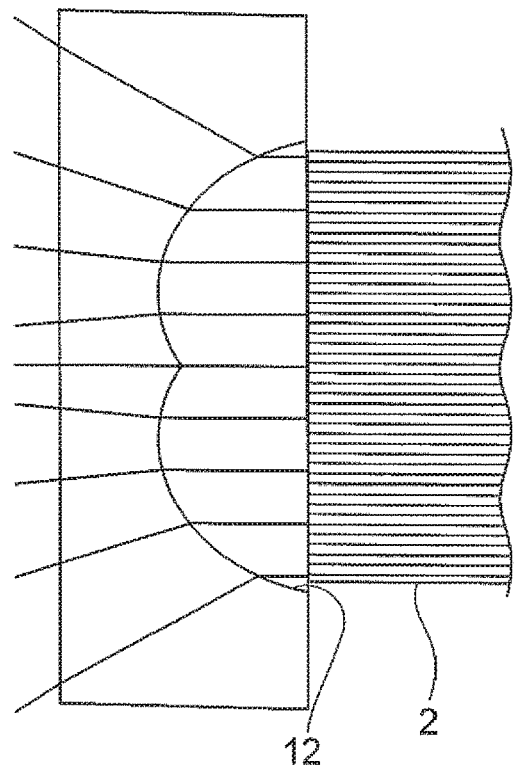
Figure 10:
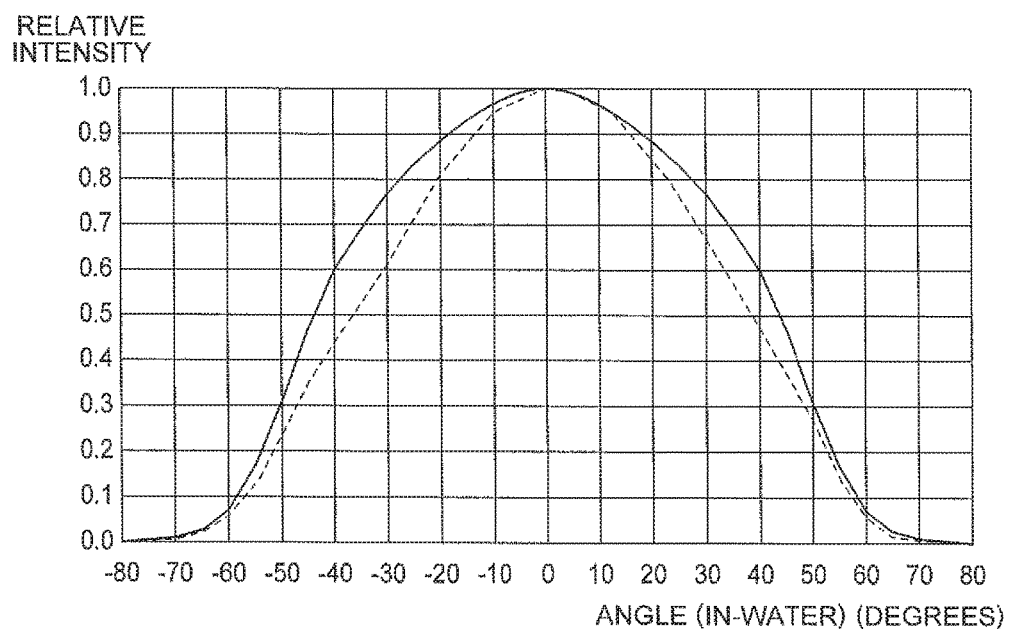
FIG. 10 is a graph showing a spherical light distribution of light emerged in water from the endoscope illuminating optical system according to the example 1.
Figure 11A:
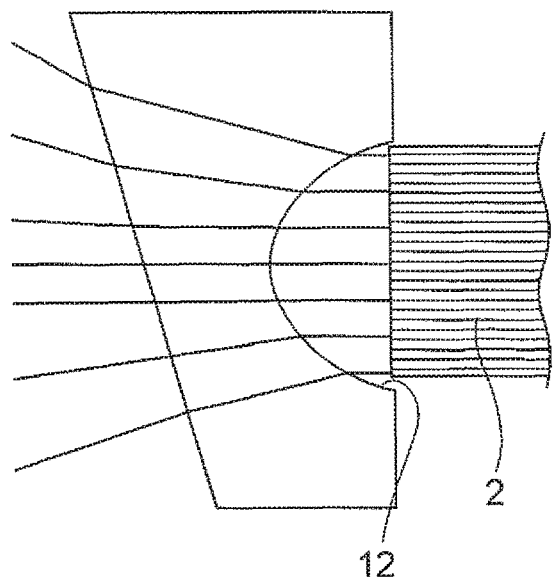
FIG. 11A and FIG. 11B are diagrams showing a cross-sectional shape of an endoscope illuminating optical system according to an example 2, where.
Figure 11B:
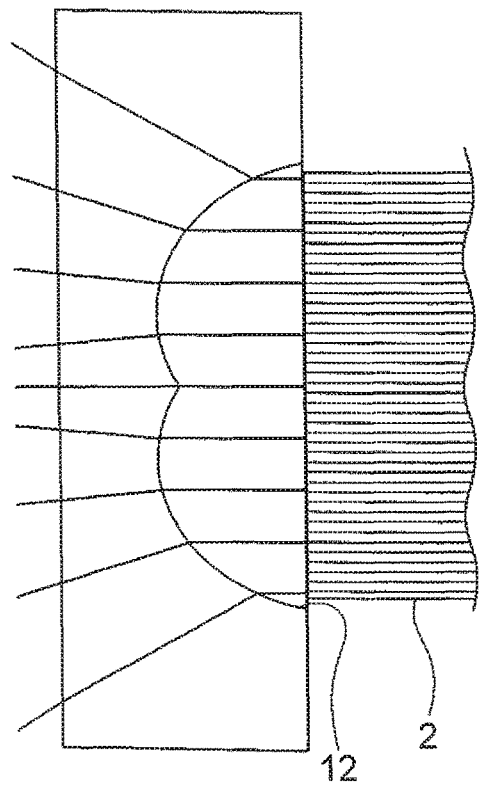
Figure 12:
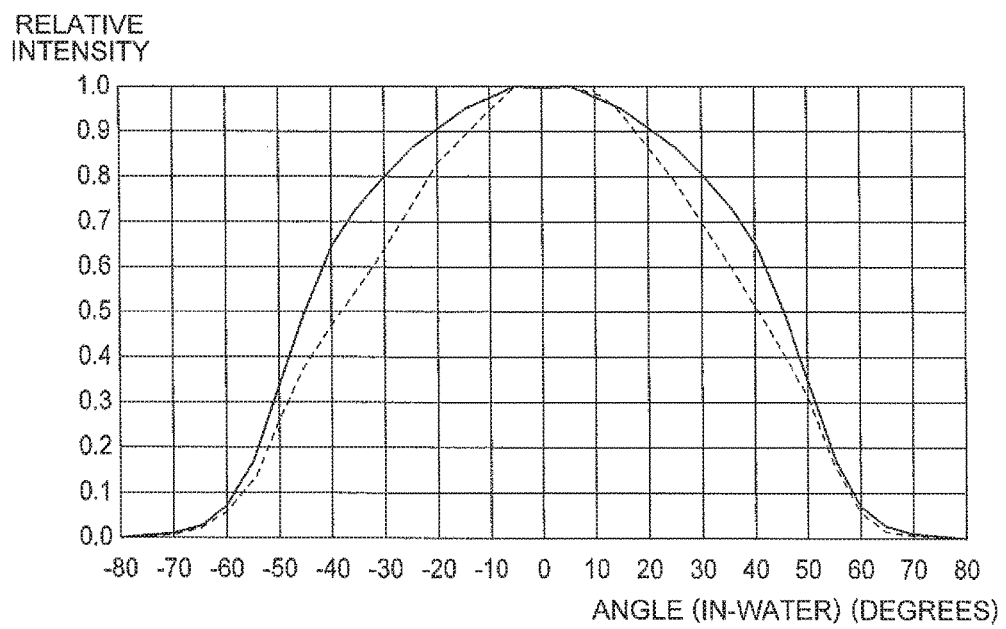
FIG. 12 is a graph showing a spherical light distribution of light emerged in water from the endoscope illuminating optical system according to the example 2.
Figure 13A:
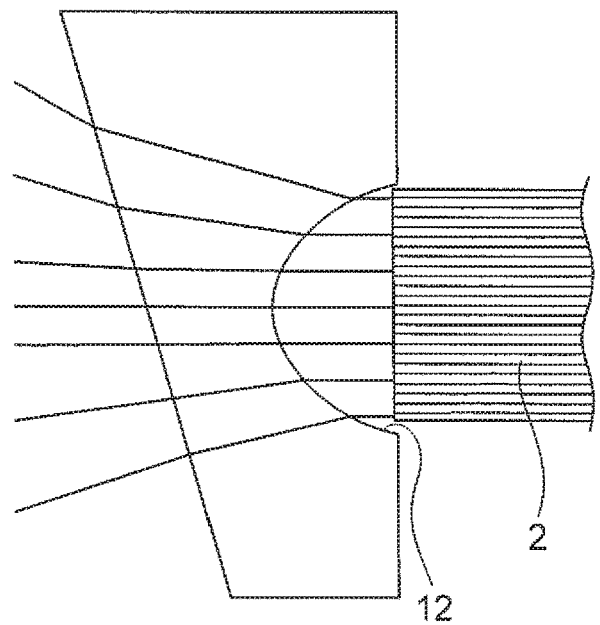
FIG. 13A and FIG. 13B are diagrams showing a cross-sectional shape of an endoscope illuminating optical system according to an example 3, where.
Figure 13B:
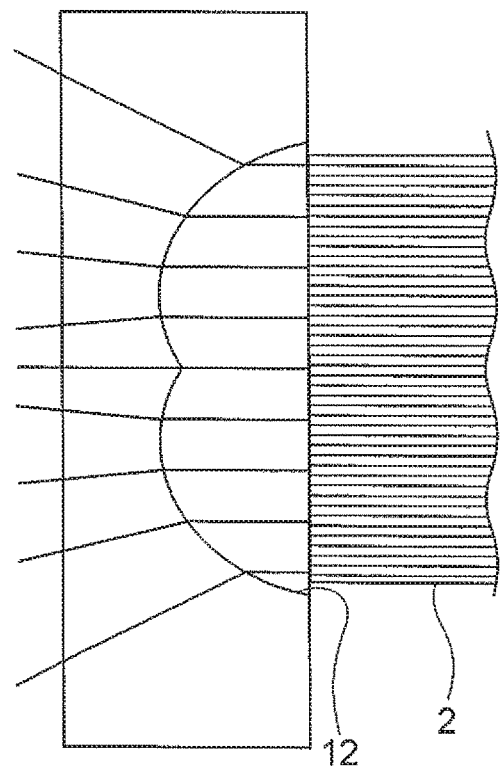
Figure 14:
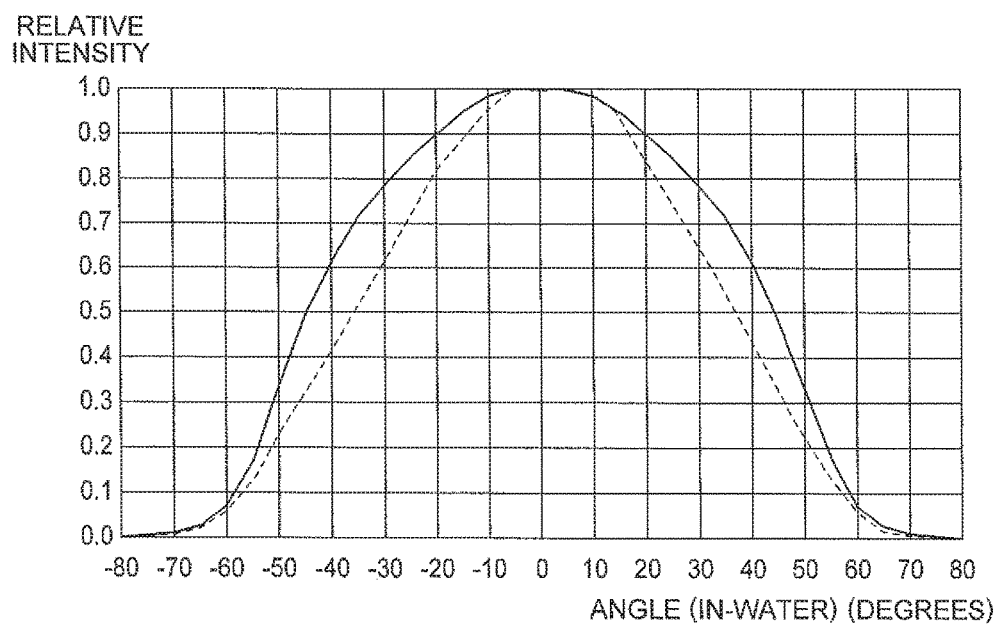
FIG. 14 is a graph showing a spherical light distribution of light emerged in water from the endoscope illuminating optical system according to the example 3.
Figure 15A:
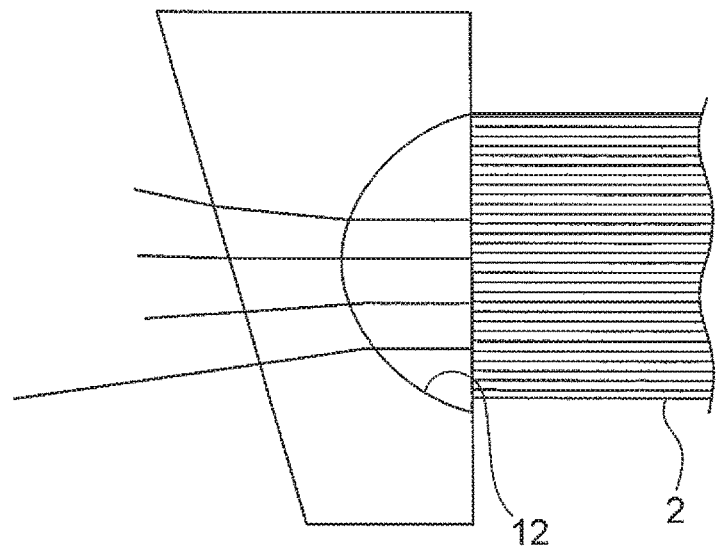
FIG. 15A and FIG. 15B are diagrams showing a cross-sectional shape of an endoscope illuminating optical system according to an example 4, where.
Figure 15B:
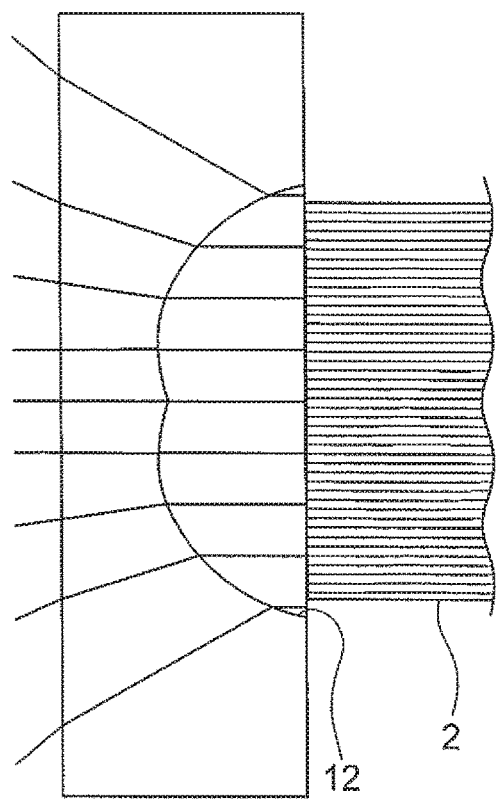
Figure 16:
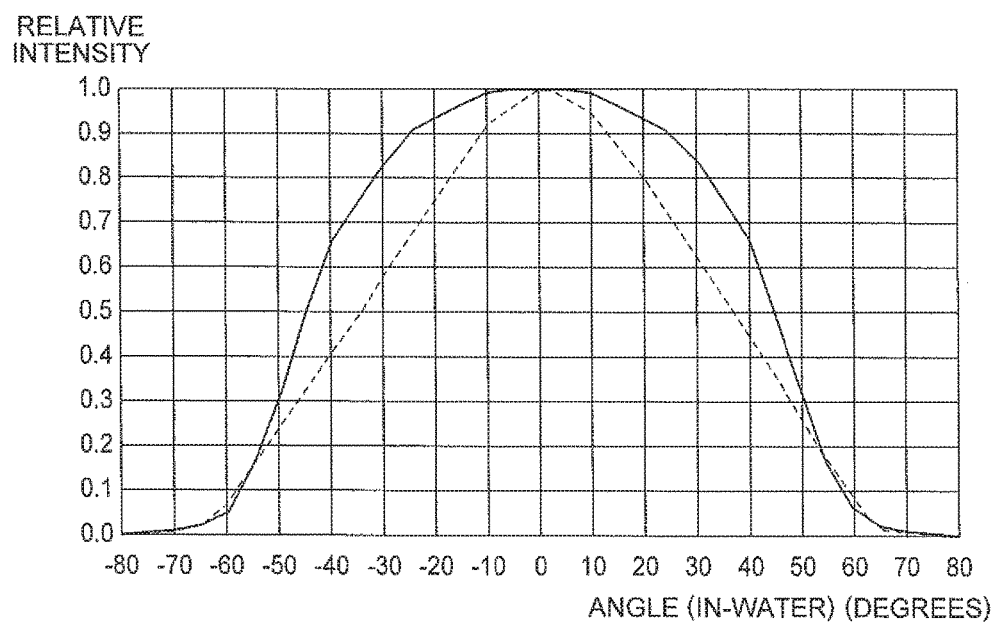
FIG. 16 is a graph showing a spherical light distribution of light emerged in water from the endoscope illuminating optical system according to the example 4.
Figure 17A:
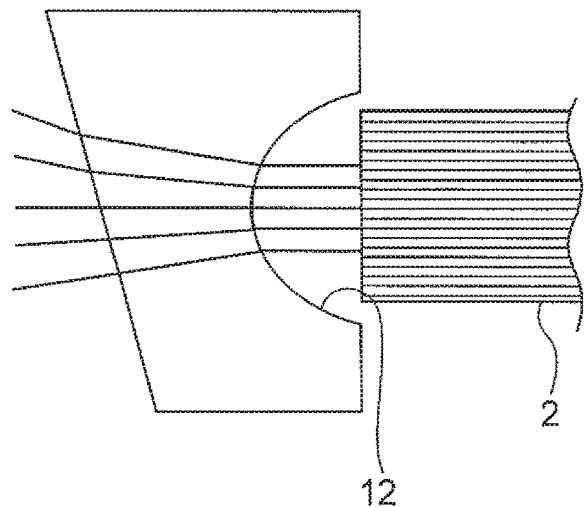
FIG. 17A and FIG. 17B are diagrams showing a cross-sectional shape of an endoscope illuminating optical system according to an example 5, where.
Figure 17B:
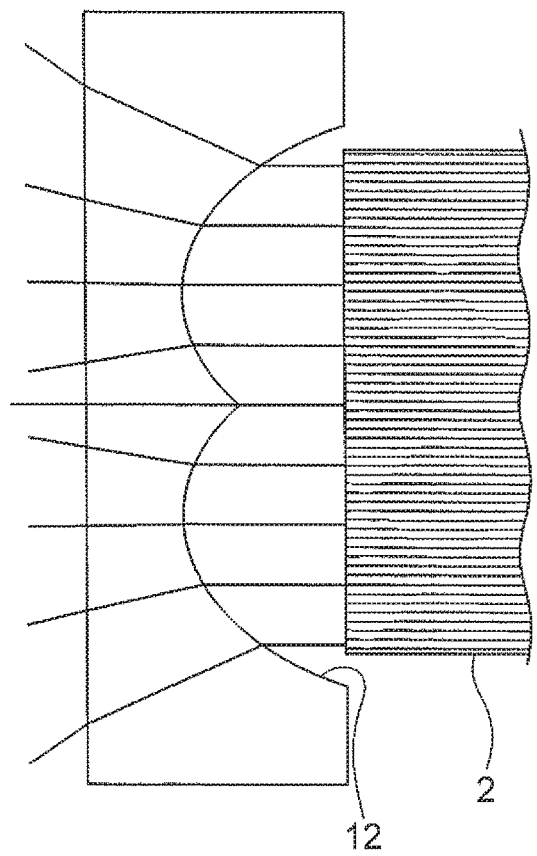
Figure 18:
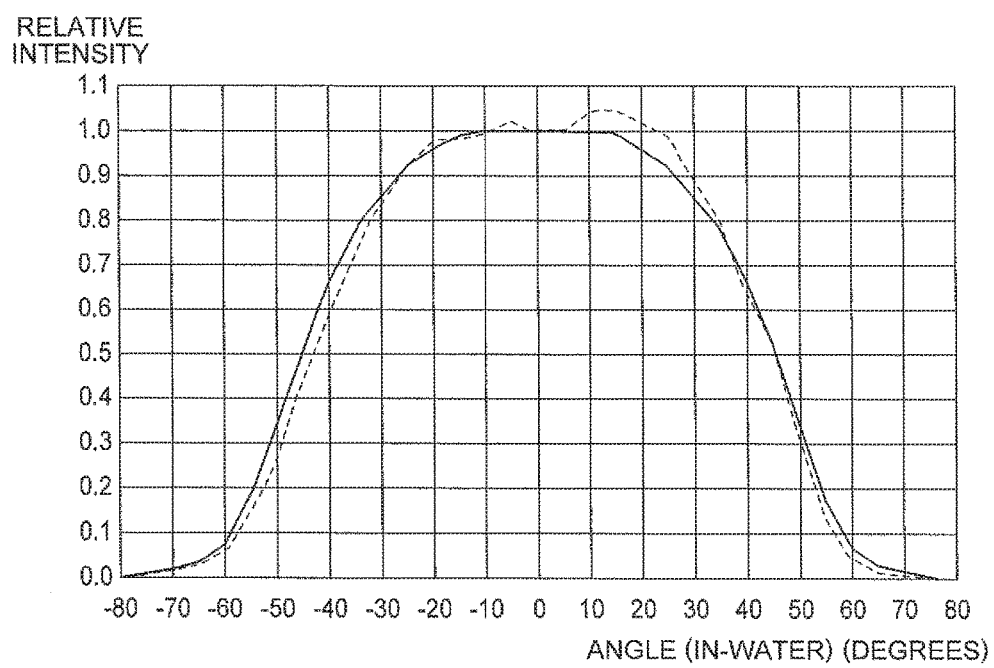
FIG. 18 is a graph showing a spherical light distribution of light emerged in water from an endoscope illuminating optical system according to the example 5.
Figure 19A:
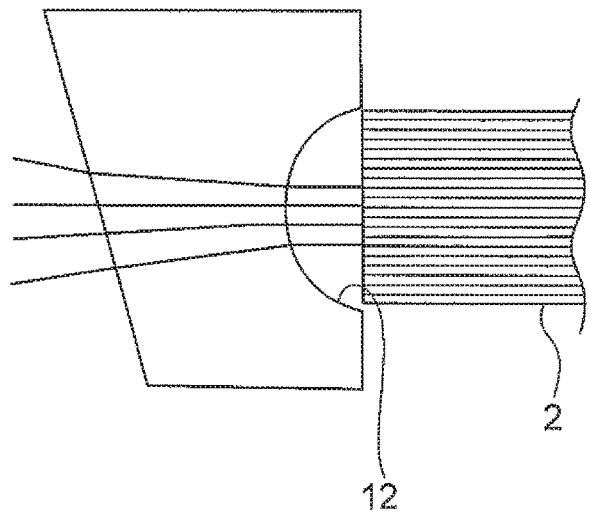
FIG. 19A and FIG. 19B are diagrams showing a cross-sectional shape of an endoscope illuminating optical system according to an example 6, where.
Figure 19B:
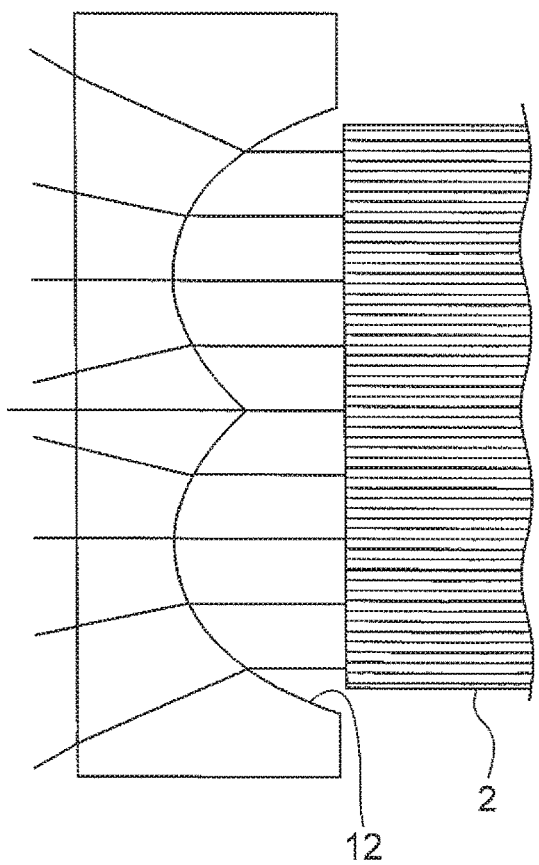
Figure 20:
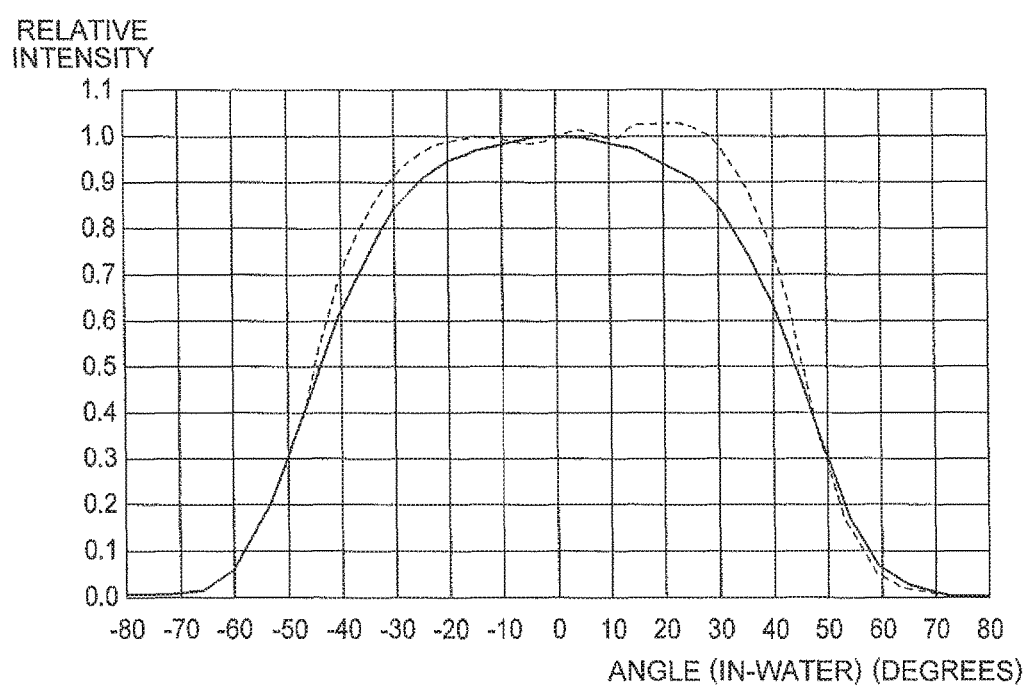
FIG. 20 is a graph showing a spherical light distribution of light emerged in water from an endoscope illuminating optical system according to the example 6.

Graphs of a cross-sectional shape of an illumination lens and spherical light distribution of light emerged in water of the examples are shown in diagrams 9A to FIG. 20. In diagrams of the cross-sectional shape, diagrams 9A and 11A shows a cross-section in the short-axis direction of a light guide, and diagrams 9B and 11B shows a cross-section in the long-axis direction of the light guide. In a graph of spherical light distribution of light emerged in water, solid line shows light-distribution characteristics in a horizontal direction and dashed line shows light-distribution characteristics in a vertical direction. Moreover, a graph of spherical light distribution is a graph in which, it is assumed that a sphere of radius 40 mm is disposed at a position away by 40 mm in water, and standardized by finding an illuminance distribution by light-beam tracking and intensity integration. Light distribution of light emerged from a light guide used for intensity integration is shown in FIG. 8.

(Regarding Illumination Lens)

A concave shape of all these examples is designed to achieve the following target spherical light distribution (proportion with respect to center) in water, assuming a visual field of slightly inner side of an in-water horizontal angle of view (118.7°) and an in-water vertical angle of view (76.3°) of the objective optical system.

Spherical light distribution in direction of 55° in water, in horizontal direction of screen: not less than 15%

Spherical light distribution in direction of 35° in water, in vertical direction of screen: not less than 50%

In all these examples, an improved light distribution which is a target is realized by optimizing the combination of a composite concave surface and a non-circular light guide, and parameters thereof, in spite of a fact that the corresponding angle of view is wide. Comparing with these examples, in an example for comparison of a circular light guide and a concave spherical lens, the desired light distribution is not achieved, and is substantially below the target as compared to that in the present embodiment both in the horizontal direction and the vertical direction.

In examples 1 to 3, the composite concave surface has the same shape, and the cross-sections of the light guides are ellipsoid, oval, and gourd-shaped respectively. Since almost same performance can be secured optically with these three types of shapes of the cross section of light guide, any of the three shapes may be used.

In examples 4 to 6, the light guides are standardized to be oval, and the degree of flatness thereof is varied. The composite concave surface in these examples is optimized according to the dimensions of the end surface of each light guide, and the shape thereof differs in each example.

In such manner, the examples 1 to 6, each having a different arrangement, satisfy conditional expressions (1) to (3), and these three conditional expressions are preferable for setting the optimum parameters. Furthermore, in all the examples, the composite concave surface includes an aspheric surface which satisfies conditional expression (4) and contributes to realization of a light-distribution target higher than that of conventional light distribution. In a case in which the in-water angle of view may be narrowed to some extent, since it is possible to lower the light-distribution target, the use of spherical surfaces as the axisymmetric concave surfaces of the composite concave surface is possible.

In such manner, according to each example, it is possible to provide an endoscope illuminating optical system in which it is possible to achieve a favorable light distribution even when the in-water angle of view is wide, and which is suitable for mounting in a medical endoscope of a thin diameter.

As described above, the present invention is useful for an endoscope illuminating optical system, and particularly for an endoscope illuminating optical system in which it is possible to achieve a favorable light distribution even when the in-water angle of view is large, and which is suitable for mounting in a medical endoscope of a thin diameter.

The present invention shows an effect that it is possible to provide an endoscope illuminating optical system in which a favorable light-distribution can be achieved even in a case of a wide in-water angle of view, and which is suitable for mounting in a medical endoscope having a thin diameter.

What is claimed is:

1. An endoscope illuminating optical system to be disposed at a front end of an insertion portion of an endoscope, the endoscope illuminating optical system comprising:
   a lens formed by a transparent-resin molding having a function of a front-end frame, which is configured to be disposed at a front-end side of the insertion portion; and
   a light guide which is disposed adjacent to the lens, wherein:
   a surface of the lens facing toward the light guide is a composite concave surface in which two axisymmetric concave surfaces are overlapped, and has a gourd-shaped effective cross-section,
   an effective range of a distal end surface of the light guide has a shape of an ellipsoid, or an oval, or a gourd, and has a long axis in a longitudinal direction of the gourd-shaped effective cross-section of the surface of the lens facing toward light guide, and a short axis in a direction perpendicular to the long axis,
   the cross-section of the composite concave surface includes the distal end surface of the light guide, and
   the endoscope illuminating optical system satisfies the following conditional expressions (1), (2), and (3):

$$1.2 < Llgl/Llgs < 4 \tag{1}$$

$$0.25 < R'/\sqrt{(Llgl \times Llgs)} < 0.6 \tag{2}$$

$$0.4 < Lofs/(Llgl - Llgs) < 1.3 \tag{3}$$

where:
Llgl denotes a maximum length in a long-axis direction of the distal end surface of the light guide,
Llgs denotes a maximum length in a short-axis direction of the distal end surface of the light guide,
R' denotes a radius of curvature at a practical center of the axisymmetric concave surfaces, and
Lofs denotes a distance between axes of the two axisymmetric concave surfaces.

2. The endoscope illuminating optical system according to claim 1, wherein the axisymmetric concave surfaces which form the composite concave surface are made of an aspheric surfaces, and satisfy the following conditional expression (4):

$$(Z(H) - Zr'(H))/R' < -0.01 \tag{4}$$

where:
$H = 0.9 \times R'$,
H denotes a height from an optical axis at the axisymmetric concave surfaces,
Z(H) denotes an amount of displacement in an optical axial direction at the height H of the axisymmetric concave surfaces, and Zr'(H) denotes an amount of displacement in the optical axial direction at the height H on a spherical surface of the radius of curvature R' at the practical center.

* * * * *